United States Patent [19]

Stubblefield et al.

[11] Patent Number: 5,204,101
[45] Date of Patent: Apr. 20, 1993

[54] METHOD AND COMPOSITION FOR TREATING ACQUIRED IMMUNODEFICIENCY SYNDROME

[76] Inventors: Thomas W. Stubblefield, 1723 Eagle Dr., Hixson, Tenn. 37343; Betty J. Cothran, 1309 Swope Dr., Chattanooga, Tenn. 37412

[21] Appl. No.: 775,596
[22] Filed: Oct. 15, 1991
[51] Int. Cl.$^5$ .................. A61K 35/78; A61K 9/48
[52] U.S. Cl. .................. 424/195.1; 424/451; 424/456; 514/885
[58] Field of Search .................. 424/195.1, 451, 456; 514/885

[56] References Cited

U.S. PATENT DOCUMENTS

| | | | |
|---|---|---|---|
| 4,795,739 | 1/1989 | Lifson et al. | 514/8 |
| 4,889,716 | 12/1989 | Keller | 424/195.1 |
| 4,921,837 | 5/1990 | Donahue | 514/2 |
| 4,985,249 | 1/1991 | Sakagami et al. | 424/195.1 |

OTHER PUBLICATIONS

Lang, Anderson, Perkins, et al.: Clinic Immunologic and Serologic Findings in Men at Risk for AIDS. *JAMA* 1987; 257:326–330.

Melmed, Taylor, Detels, et al.: Serum Changes in HIV Infected Subjects: Indicators of Significant Pathology, CD4 T-cell Changes and the Development of AIDS. *J AIDS* 1989; 2:70–76.

Gallo, Diggs, Shell, et al.: Comparison of Detection of Antibody to AIDS Virus by Enzyme Immunoassay, Immunofluorescence, and Western Blot Methods. *J. Clin Microbiol* 1986; 23:1049–1051.

Constituents of Phytolacca Species. II. Comparative Examination of Constituents of the Roots of Phytolacca Americana, P. Esculenta and P. Insularis. Woo, W.S.: Chi, H. J.: Kang, S. S. Annu Rept Nat Prod Res Inst Seoul Natl Univ 15:107–(1976). (Nat Prod Res Inst Seoul Natl Univ Seoul South Korea).

Constituents of Phytolacca Species. III. Components of Over-Ground Parts and Callus Tissues. Woo, W. S.: Kang, S. S. Annu Rept Nat Prod Res Inst Seoul Natl Univ 15:111–(1976). (Nat Prod Res Inst Seoul Natl Univ Seoul South Korea).

Anatomical and Histochemical Investigations on Some Species of the Genus Rumex. Milkowska, J.: Krzaczek, T.: Przychodzen, A.: Ann Univ Mariae Curie-Sklodowska Sect D Med 30: 225–232 (1975). (Zakl Bot Farm Inst Anal Technol Farm Akad Med Lublinie Poland).

Screening for Antimicrobial and Presumed Cancerostatic Plant Metabolites. Dornberger, K.: Lich, H.: Pharmazie 37: Wissenschaften Der Ddr, Forschungszentrum fur Molekularbiologie und Medizin Jena Germany).

Insolation and Identification of Vitamin C. Waugh, W. A.: King, C. G., Nutr Rev 34:81–(1976) (Dept Chem Univ Pittsburgh Pittsburgh Pa. 15213 USA).

Structure and Hypotensive Effect of Flavonoid Glycosides in Lemon Peeling. (part II). Kumamoto, H.: Matsubara, Y.: Iizuka, Y.: Okamto: Yokoi, K.: Nippon Nogei Kagaku Kaishi 59 7: 677–682 (1985) (Fac Sci Eng Kinki Univ Higashi Osaka 577 Japan).

*Primary Examiner*—John W. Rollins
*Attorney, Agent, or Firm*—Joseph P. Nigon

[57] ABSTRACT

A method and composition for treating Acquired Immunodeficiency Virus infections with a composition formulated from dried powders of *Phytolacca americana*, *Rumex acetosella* and *Rutacea liminonia*. The resulting composition acts as an anti-viral agent.

3 Claims, No Drawings

METHOD AND COMPOSITION FOR TREATING ACQUIRED IMMUNODEFICIENCY SYNDROME

BACKGROUND OF THE INVENTION

The present invention relates to a plant derived pharmaceutical composition that has anti-viral HIV activity. The human immunodeficiency virus (HIV) is the causative agent associated with acquired immune deficiency syndrome (AIDS). AIDS and a less malignant form of the lethal disease AIDS Related Complex (ARC), and other related maladies respond to treatment with the composition of this invention.

AIDS was originally defined by the Centers for Disease Control as a disease at least moderately predictive of a defect in a cell mediated immunity, occurring in a person with no known cause for diminished resistance to the disease. It is now known that the syndrome AIDS is simply the end-stage manifestation of a prolonged, chronic erosion of the immune system caused by HIV. The syndrome defined term AIDS may be an outdated term. Perhaps the term "late stage HIV infection" may be a better term since it emphasizes the concept that HIV causes a spectrum of diseases.

HIV infection is a disease of the immune system just as hepatitis B is a disease of the liver, and influenza virus is a disease of the lung. Acute infection with HIV is usually asymptomatic but around the time of seroconversion one fourth of patients may experience transient low grade fever, malaise and other non-specific constitutional symptoms sometimes accompanied by a diffuse erythematous macropapular rash. The patient remains asymptomatic throughout most of the clinical course of the HIV infection. Despite an absence of symptoms about one half of asymptomatic patients develop clinically detectable diffuse enlargements of the lymph nodes. Disease progression is marked by a steady decline in the number of T-helper lymphocytes (CD4 lymphocytes). Other hematological abnormalities include dysregulation of antibody production by B-cells and hypergammaglobulinimia.

When the CD4 lymphocyte count falls below 200 cells per cubic millimeter, most patients begin to have symptoms and/or show clinical evidence of the disease. For reasons poorly understood clinically overt manifestations of disease usually appear on the mucocutaneous surface. Oral thrush (candidiasis) is the most widely recognized harbinger of systemic opportunistic infection, but a variety of other dermatological conditions may appear. Onset of fever, weight loss, night sweats or other constitutional signs signal the occurrence of a serious systemic opportunity infection or AIDS.

SUMMARY OF THE INVENTION

It is therefore an object of the present invention to provide a method and composition for treating HIV infections.

It is thererfore, an object of the present invention to provide a method and composition for eliminating the signs and symptoms which are characteristic of HIV infections.

It is, therefore, an object of the present invention to provide a method and composition for restoring the hematological profile of the host.

It is, therefore, an object of the present invention to provide a method and composition for providing immunological improvement in the patient, i.e., restoring to the host their immune system.

DETAILED DESCRIPTION OF THE INVENTION

It has been discovered that if an HIV infected patient with AIDS is administered a compound mixture of constituents found in two naturally occurring plants, i.e., *Rumex acetosella* and *Phytolacca americana* and a naturally occurring fruit, i.e. *Citrus limonia* a substantial improvement in the condition of the patient.

The three plants are identified as:

COMMON NAME: Sheep Sorrel
FAMILY: Polygonaceae (Buckwheat)
GENUS: Rumex
SPECIES: *acetosella*

COMMON NAME: Pokeweed or pokeberry
FAMILY: Phytolaccaccea
GENUS: Phytolacca
SPECIES: *americana*

COMMON NAME: Lemon
GENUS: Citrus
FAMILY; Rutaceae
SPECIES; *limonia*

The chemical constituents of the plants are well known and are discussed in detail in several publications. Typical of the publications relating to *Phytolacca americana* are:

Constituents of Phytolacca Species. II. Comparative Examination
 of Constituents of the Roots of *Phytolacca americana*. *P. esculenta* and *P. insularis*.
 WOO, WS: Chi, HJ: Kang, SS.
 Annu Rept Nat Prod Res Inst Seoul Natl Univ 15:107–(1976)
Constituents of Phytolacca Species. III. Components of Over-Ground
 Parts and Callus Tissues.
 Woo, WS and Kang, SS.
 Annu Rept Nat Prod Res Instut Seoul Univ 15: 111–(1976)
Typical publications relating to *Rumex acetosella* are:
Anatomical and Histochemical Investigations Of Some Species of
 the Genus Rumex.
 Milkowska J, Krzacek T and Przychodzen A.
 Ann Mariae Curie-Sklodowska Sect D Med, 30 225–232, (1975)
Screening for Antimicrobial and Presumed Cancerostatic Plant
 Metabolites.
 Dornberger,K: Lich, H:
 Pharmazie 37: 215–221 (1982)
Typical publications relating to *Citrus limon* are:
Isolation and Identification of Vitamin C.
 Waugh, WA: King, CG:
 Nutr Rev 34: 81–(1976)
Structure and Hypotensive Effect of Flavenoid Glycosides in
 Lemon Peelings. (Part II).
 Kumamoto, H: Matsubara, Y: Iizuka,K: Yokoi,K;
 Nippon Nogei Kagaku Kaishi 59 7: 677–682 (1985).
 Fac Sci Eng These publications are incorporated herein by reference.

For purposes of this invention it should be understood that the desirable results of the treatment of this invention is the effected by the three plants. It is believed that the synergistic effect of the three plants plays a vital role in the anti-viral action.

PREPARATION OF THE PLANTS

Each plant is first dried in a dehydrator so that a more concentrated form of the active chemical constituents is obtained. The entire plant, i.e. the roots, stem, petiole, leaves seeds and flower is dried. In the case of the lemon, the fruit portion including the seeds and peeling are dried. The lemon is cut into slices about one eighth inch in thickness for the drying process.

Both the sheep sorrel and pokeweed leaves are dried at a temperature between 95 to 105 degrees Fahrenheit. The lemon slices and the pokeweed purple berries are dried at a temperature between 130 and 135 degrees Fahrenheit. Once dried the "plant" material should be stored in a deep freezer in individual airtight containers and should be protected from light.

The dried materials are reduced to a moderately fine sized powder using any conventional technique, just before use. No material should be used that has been in storage more than two years.

All three plant powders are kept segregated before being mixed. In the preferred procedure the powders are mixed equally ($\frac{1}{3}$, $\frac{1}{3}$, $\frac{1}{3}$) by weight and placed in gelatin capsules for administration.

ROUTES OF ADMINISTRATION: There are two primary routes of administration, namely, oral and rectal. The suppository route may give better results. However, it may be advisable, in cases of severe diarrhea to administer the composition orally.

DOSAGES: In the preferred procedure the dosage regimen as a total daily administration should be in the range of 1 to 40 milligrams per kilogram of body weight per day. An especially preferred dosage is in the range of 7 to 12 milligrams of the composition per kilogram of body weight per day. The total daily dosage should be divided into equal portions and be given 12 hours apart. Progress can be monitored by periodic assessment of the hematological profile, CD4 lymphocytes count, reticulocyte count or platelet count.

These tests are conventional blood tests described extensively in the literature. Two such references are:
- Lang, Anderson, Perkins et al: Clinical Immunologic and Serologic Findings in Men at Risk for AIDS. JAMA 1987: 257:326–330.
- Melmed, Taylor, Detels, et al: Serum Changes in HIV Infected Subjects: Indicators of Signifigant Pathology, CD4 T-cell Changes and the Development of AIDS. *J AIDS* 1989; 2:70–76

The Western Blot test is a standard diagnostic test for HIV infections. The test is described in:
- GAllo, Diggs, Shell et al: Comparison of Detection of Antibody to HIV by enzyme immunoassay, immunofluoresence and Western Blot Methods. J Clin Microbiol 1986; 23: 1049–1051.

These publications are incorporated herein by reference.

The dosage regimen and mixture ratio may be altered by the attending physician upon consideration of the patient's overall condition, the severity of the infection, and other clinical factors.

The efficacy of the method and composition of the instant invention is apparent from the following clinical data.

Case 1

A 25 year old white male was found to be HIV positive after a long exposure to multiple sexual partners. He gave no history of IV drug use nor had he ever received a blood transfusion. His weight was 138 pounds. He had first been found to be HIV positive confirmed by the Western blot test and the T4 lymphocyte count had declined to 200 cells per cubic millimeter. He had also experienced significant weight loss, persistent fever and diarrhea over the past six months. He was anemic, neutropenic, and thrombocytopenic.

He was initially given one capsule daily for a week, then gradually increased at weekly intervals until he was taking 2 capsules 3 times a day. His T4 lymphocyte count and complete blood count (CBC) were rechecked at weekly intervals and no significant change was appreciated until after 14 weeks. After that period of time he began to feel an increase in his sense of well being along with a slight increase in his weight. At 28 weeks his CBC improved in the parameters mentioned above and his T4 lymphocyte count began to improve. After 32 weeks it was 780. By this time his weight had increased 15 pounds. He no longer was having fever or diarrhea.

CASE 2

A 32 year old black male was found to be HIV positive and admitted to a homosexual life style along with IV drug use for 5 years. His disease was confirmed by the Western blot and his T4 lymphocyte count was 520 cells per cubic millimeter. His CBC, platelet count, biochemistry profile including liver function tests and erythrocyte sedimentation rate were all with-in normal limits. Three months earlier he had developed oral candidiasis that was very resistant to multiple modes of therapy. He had not experienced any significant weight loss from his normal 168 pounds.

He was initially given one capsule per day and the dosage was increased at weekly intervals until he was taking 2 capsules 3 times a day. The oral candidiasis which had troubled him for 3 months slowly over a period of 6 weeks resolved. His T4 lymphocyte count increased from a pretreatment level to 520 to 800.

CASE 3

A 29 year old male who was HIV positive for approximately 48 months, denied homosexual behavior, illicit drug use and allegedly had never received a blood transfusion. He did admit to having spent the past 6 years in state prison. His disease was confirmed by the Western blot and his T4 lymphocyte count was 355 cells per cubic milligram. He had experienced a 25 pound weight loss and one episode of aseptic meningitis. Since the episode of meningitis he had developed forgetfulness, loss of concentration, lethargy, and loss of balance.

He was given one capsule a day for a week and the dosage was increased at weekly intervals until he was taking 2 capsules 3 times a day. Blood work was done at weekly intervals and within 8 weeks his blood pictures started to improve. By the end of 16 weeks his T4 lymphocyte count had increased to 470. His neurological symptoms had all but disappeared and he had gained 14 pounds.

CASE 4

A 38 year old white male homosexual was found to be HIV positive at age 28. He apparently had experienced good health until 6 months prior to being diagnosed by his personal physician as having developed persistent herpes simplex infection, chronic diarrhea, weight loss, and a chronic cough. His disease was confirmed by the Western blot and his T4 lymphocyte count was 190 cells per cubic millimeter. He subsequently developed pneumocystis carinii pneumonitis.

He was initially given one capsule a day for a week and the dosage was increased at weekly intervals until he was taking 2 capsules 3 times a day. Blood work was done at weekly intervals and his T4 lymphocyte count increased to 300 after 12 weeks of therapy. His cough persisted. He was lost to follow-up. It is not known whether he expired or simply moved out of the area.

CASE 5

A 46 year old black homosexual male was found to be HIV positive 8 years previously. His disease was confirmed by the Western blot and his T4 lymphocyte count was 108 cells per cubic millimeter. He had been recently hospitalized with tuberculosis and had lost considerable weight over the last year.

He was initially given 2 capsules a day for a week and rapidly increased to 3 capsules 3 times a day within a month due to his seemingly rapid deterioration. Within 6 weeks of therapy he started to feel better and within 10 weeks his T4 lymphocyte count was 378. By 16 weeks of therapy he had gained 20 pounds and his lymphocyte count was 654.

What is claimed is:

1. A method of increasing the T4 lymphocyte counts of patients testing positive for human immunodeficiency virus consisting essentially of administering to the patients about 1 to 40 milligrams of a composition consisting of approximately equal amounts of dried powdered *Phytolocca americana*, *Rumex acetosella* and *Citrus liminonia*, on a daily basis.

2. A method of increasing the T4 lymphocyte counts of patients testing positive for human immunodeficiency virus consisting essentially of administering to the patients capsules containing about 7 to 12 milligrams of a composition consisting of equal amounts of dried powdered *Phytolocca americana*, *Rumex acetocella* and *Citrus liminonia*, on a daily basis.

3. As a composition of matter a formulation for increasing the T4 lymphocyte count of patients testing positive for human immunodeficiency virus consisting of equal amounts of dried powdered *Phytolocca americana*, *Rumex acetosella* and *Citrus liminonia*.

* * * * *